United States Patent
Komatsu et al.

[11] Patent Number: 5,863,789
[45] Date of Patent: Jan. 26, 1999

[54] MICROORGANISM-HOLDING CARRIER AND METHOD FOR REMEDIATION OF SOIL EMPLOYING THE CARRIER

[75] Inventors: Toshiyuki Komatsu, Hiratsuka; Masanori Sakuranaga; Tsuyoshi Nomoto, both of Atsugi; Shinya Kozaki, Tokyo; Takeshi Imamura, Chigasaki, all of Japan

[73] Assignee: Canon Kabushiki Kaisha, Tokyo, Japan

[21] Appl. No.: 899,707

[22] Filed: Jul. 24, 1997

Related U.S. Application Data

[63] Continuation of Ser. No. 314,004, Sep. 28, 1994, abandoned.

[30] Foreign Application Priority Data

Sep. 30, 1993 [JP] Japan .................................. 5-243447
Nov. 2, 1993 [JP] Japan .................................. 5-274079
Nov. 16, 1993 [JP] Japan .................................. 5-286763

[51] Int. Cl.$^6$ ...................................................... C12S 13/00
[52] U.S. Cl. .................. 435/262; 435/262.5; 435/178; 435/179; 435/180; 435/244; 435/245; 71/64.11
[58] Field of Search .............................. 435/262, 262.5, 435/174, 176–182, 189, 244, 245; 71/6, 64.11, 64.13; 424/405, 417, 450, 93.1, 93.47

[56] References Cited

U.S. PATENT DOCUMENTS

| | | | |
|---|---|---|---|
| 3,740,315 | 6/1973 | Li et al. ................................... | 435/262 |
| 3,897,308 | 7/1975 | Li et al. ................................... | 435/262 |
| 4,266,030 | 5/1981 | Tchang et al. ........................... | 435/180 |

(List continued on next page.)

FOREIGN PATENT DOCUMENTS

| | | |
|---|---|---|
| 0-090652 | 10/1983 | European Pat. Off. . |
| 0-095049 | 11/1983 | European Pat. Off. . |
| 0200297 | 11/1986 | European Pat. Off. . |
| 3613575 | 10/1987 | European Pat. Off. . |

(List continued on next page.)

OTHER PUBLICATIONS

R. Vargas, et al., "Protozoan Predation of Bacterial Cells in Soil Aggregates", FEMS Microbiology Ecology, vol. 38 (1986), pp. 233–242.

French et al., "Lignin Degration in the Termites", Mater Org. (Berl.) vol. 10 (4), pp. 281–288, 1975.

Lee, K.E. et al., "Termites and Soils"; Publisher: Academic Press, pp. 128–145, 1971.

O'Brien et al., "Role of Microorganisms in the Metabolism of Termites", Aust. J. Biol. Sci., vol. 35, 239–62, 1982.

Lee, M.J., Association of Methanogenic. . . . . Hindgut, Current Microbiol., vol. 15, pp. 337–341, 1987.

Odelson, et al., "nutrition and Growth . . . . Termites", Appl. & Environ. Microbiol., vol. 49 (3), pp. 614–621, 1985.

Stone et al., "A Structural Model . . . . Macromolecules", Cellulose Chem., & Techn. 2, 343–358 (1968).

(List continued on next page.)

*Primary Examiner*—William H. Beisner
*Attorney, Agent, or Firm*—Fitzpatrick, Cella, Harper & Scinto

[57] ABSTRACT

A carrier for holding a microorganism in soil releases, from a constituting material thereof, an inducer for production of an enzyme of the microorganism for soil remediation. The carrier for holding a microorganism may comprise a combination of a microorganism holding carrier composed of a hydrophilic polymer for holding the microorganism with an inducer-holder composed of another polymer for holding inducer manifesting a biological action to the microorganism adjacent to each other. A method for remediation of soil comprises application of the microorganism-holding carrier into the soil. A soil-remedying agent comprises the microorganism-holding carrier and a microorganism held thereon which exhibits enzyme activity for decomposition of a polluting substance in the soil under action an inducer released by the carrier.

25 Claims, 4 Drawing Sheets

U.S. PATENT DOCUMENTS

| | | | |
|---|---|---|---|
| 4,332,904 | 6/1982 | Kurane | 435/262 |
| 4,456,685 | 6/1984 | Guthrie | 435/109 |
| 4,535,061 | 8/1985 | Chakrabarty | 435/253 |
| 4,556,623 | 12/1985 | Tamura et al. | 430/83 |
| 4,859,594 | 8/1989 | Portier | 435/172.1 |
| 4,871,673 | 10/1989 | Rehm et al. | 435/262 |
| 4,925,802 | 5/1990 | Nelson et al. | 435/262 |
| 5,188,837 | 2/1993 | Domb | 424/450 |
| 5,202,227 | 4/1993 | Matsuda et al. | 430/230 |
| 5,219,926 | 6/1993 | Lindman et al. | 525/54.1 |
| 5,284,587 | 2/1994 | Wong et al. | 210/606 |
| 5,294,491 | 3/1994 | Goeldner et al. | 428/402 |

FOREIGN PATENT DOCUMENTS

| | | |
|---|---|---|
| 567102 | 10/1993 | European Pat. Off. . |
| 0594125 | 4/1994 | European Pat. Off. . |
| 2501229 | 9/1982 | France . |
| 2752380 | 5/1979 | Germany . |
| 44-20389 | 9/1969 | Japan . |
| 6-22769 | 2/1994 | Japan . |
| 90-01465 | 2/1990 | WIPO . |
| 90-10079 | 9/1990 | WIPO . |
| 92-19738 | 11/1992 | WIPO . |

OTHER PUBLICATIONS

Masque, et al. "Biotech. Letters", 9, 9 (1987), 655–660.
Skryabin, et al. "Conversion of Org. Compound by Microorganism", p. 287. (No date provided).
J. French, "The Role of Termite", Material and Organism 10, 1 (1975), p. 7–13.
Shields et al., "Mutants of Pseudomonas", Appl. & Environ. Microb., 57, 7, (1991) 1935–1941.
Database WPI, Week 9151, Derwent AN 91–373416 (1991).
Sasaki et al., "Functional Film and Production Thereof", Abstract of JP 01–110551, Apr. 27, 1989.
Oishlik, "Immobilized Enzyme", Abstract of JP–5–15372, Jan. 26, 1993.
Abstract, DerwentWPI 85–211344135, JP 93–68499. (1996).
Section Ch. Week 9322, Derwent, Class D15, AN 92–273643. (1992).
Cellulose Resources, Koejima, Gakkai Shippon Center, 100–116. (No date provided).
Chem. Abstr., vol. 108, No. 2, Abstr. 10677p, Jan. 1988.
Chem. Abstr., vol. 107, No. 19, Abstr. 170091a, Nov. 1987.
Database WPI, Section Ch, Week 9151, Derwent Publications for JP 3–251178, Nov. 1991.
Asahi Chem, STN. WPIDS Abstract No. 80–46995c of JP 55066501 May 20, 1980.

MICROORGANISM-HOLDING CARRIER AND METHOD FOR REMEDIATION OF SOIL EMPLOYING THE CARRIER

This application is a continuation of application Ser. No. 08/314,004 filed Sep. 28, 1994, now abandoned.

BACKGROUND OF THE INVENTION

1. Field of the Invention

The present invention relates to a carrier for immobilization of a microorganism for remediation of soil. The present invention also relates to a method for remediation of soil employing the carrier holding the soil-remedying microorganism.

The present invention further relates to a microorganism-immobilizing carrier for a bioreactor system, a biosensor, and an artificial internal organ utilizing the biological activity of an immobilized microorganism, in particular, to a microorganism-mobilizing carrier which is capable of exhibiting biological activity and improving survivability of the microorganism.

2. Related Background Art

In recent years, various noxious and hardly-decomposable chemical substances have been detected in soils, in rivers, in seas, and in the air, and aggravation of the pollution with such substances is attracting attention. In particular, soil pollution by organic chlorine compounds is causing serious problems. Establishment of techniques for preventing the spread of the pollution and for remedying the polluted environment is strongly desired. For example, soil pollution has become a matter of concern in gas production sites, oil refinery sites, demolished oil refinery sites, demolished fuel stockyard sites, demolished pulp plant sites, etc. Therefore development of soil remediation technique is strongly desired to clean the polluted soils.

The pollution of the soil not only prevents subsequent use of the land but also is liable to cause spreading of the polluted area by diffusion of the polluting substance into underground water and its diffusion with the water. Therefore a soil remediation technique is earnestly desired to be developed early.

Various soil remediation methods are known and have been tried to restore the soil to the original state by removing the polluting substance from the polluted soil.

The methods include physicochemical methods such as aspiration of the polluting substance from the soil by vacuum extraction. The physicochemical methods, however, involve many problems such as high cost, low operability, difficulty in treating the polluting substance existing at a low concentration.

On the other hand, soil remediation utilizing a microorganism, namely bioremediation, is promising.

The bioremediation methods include strengthening of self-cleaning function of ecosystem by activating a native microorganism in the soil to decompose the polluting substance into an innoxious substance; and include also, as an improved method, intentional introduction of microorganism having the ability to decompose the polluting substance from the outside to accelerate the remediation of the polluted soil.

Many kinds of microorganisms are known which have ability of decomposing the polluting substances detected in the soils. Direct application of such a microorganism to the soil does not give usually the intended cleaning effect because the applied microorganism individuals rapidly decrease in number in the soil in a short period.

To solve the problem of rapid decay of the applied microorganism in the soil, a large amount of nutrients for the applied microorganism may be introduced to the soil. This requires a high cost and may cause secondary pollution with the nutrients. Therefore, a method is demanded for maintaining the remediation activity by prolonging the life of the microorganism in the soil without supplying a large amount of the nutrients.

The change of the number of microorganism cells applied to the soil is greatly affected by the water content and the nutrient content of the soil. The amounts of water and the nutrients in the soil depend on the location of the soil, the landform, the vegetation on the soil, the depth, and the soil composition. These factors greatly affect the physiological activity of the microorganism growing in the soil. The situation is the same in the polluted soil.

For example, if the water content of the soil, more correctly the content of water available to the applied microorganism, is not in the range suitable for the microorganism, the applied microorganism usually does not grow well or does not manifest satisfactory activity. If the water content in the environment is deficient, the activity of the microorganism drops: a decomposing microorganism decreases its decomposition activity. At further deficiency of the water, a microorganism having no drought-resistance decreases in number and finally dies, whereas a drought-resistant microorganism also forms spores or goes into a dormant state to exhibit extremely low activity, whereby the decomposition of the noxious substance is not achieved. On the contrary, if the water in the environment is excessive, the oxygen content in the water becomes deficient, and an aerobic microorganism decreases its activity or decreases the number of microorganism cells. Since most of the microorganism having high activity in decomposing polluting substances are aerobic, the oxygen-deficiency is usually undesirable.

Another cause of decrease of the microorganisms in the soil is competition between the applied microorganism and native microorganisms, particularly predation of applied microorganism by protozoa. Suppression of the predation is necessary to improve the survivability of the applied microorganism.

On the other hand, in addition to the improvement of survivability of the applied microorganism, the bioremediation involves another problem on efficiency of diffusion of the applied microorganism in the soil. The bioremediation is directed to a polluted land over a large area which contains a pollutant at a low concentration, and therefore cannot be treated by a physicochemical method such as vacuum extraction. To clean such soil practically, the decomposing microorganism is required to diffuse in the polluted soil. However, the microorganism cannot easily migrate in the soil. Therefore, a method needs to be developed for bringing the microorganism to the proximity to the polluting substance in the soil. Currently conducted methods include injection of a decomposing microorganism into soil by pressure of water or air, application of a large amount of a decomposing microorganism, and so forth. With such a method, however, the diffusion of the microorganism is extremely impeded in some kinds of soils such as soils of a high clay content or of a low water content. Therefore, an improved method is required.

Some pollutant-decomposing microorganisms require coexistence of a low molecular weight compound called an inducer that induces expression of the enzyme. For example, Methylocystis sp. M strain does not decompose TCE (trichloroethylene) until the methane monooxygenase activity is induced by the presence of methane. Pseudomonas cepacia KK01 strain (Deposit No. FERM BP-4235) described in Japanese Patent Application No. 4-103180 decomposes TCE by appearance of toluene-monooxygenase induced by the presence of phenol.

As described above, the biodegradation of noxious substance in the soil or underground water from the polluted soil is conducted usually by a specific decomposing microorganism by co-oxidation or a like mechanism. Therefore, methods are tested or considered which introduce the required substance such as methane or phenol from the outside into the soil. Such methods, however, not only accompany other danger (e.g., inflammation, pollution, etc.) caused by the introduced substance but also cause diffusion of the introduced substance into a larger area or into the air or retention of the substance for a long term by adsorption by soil, which are therefore not practicable.

A method is studied in which the microorganism is mutated by gene technology so as not to require any inducer. In the open system for soil remediation, however, confirmation of safety and legal control of this method are not sufficient and thus, the method is not practicable at present.

Production of useful materials or treatment of waste materials by use of biological activity are widely conducted as a bioreactor. The employed organism includes prokaryote, eukaryote, and recombinant thereof, and is selected therefrom depending on the object. Immobilization of the microorganism in a high density is effective to mitigate mechanical shocks to the organism, to conduct recovery of the product efficiently, and to conduct the treatment continuously. The microorganism-immobilizing carrier investigated for such purposes includes polysaccharides, agarose, alginate gels, acrylamide gels, collagen, and synthetic material modified chemically to have increased suitability for organisms. The method of immobilization of the microorganism includes incorporation by solidification of a polymer, polymerization, or chemical crosslinking with a bonding agent.

The nutrients for growth need to be supplied to the immobilized microorganism by diffusion from outside the immobilizing carrier such as immersion of the microorganism-immobilizing carrier in a liquid culture medium.

In order to maintain the activity of the immobilized microorganism for a long term, an inducer and minerals have to be added by diffusion from the outside in the same manner as the aforementioned nutrients. The inducer is required to be supplied constantly because it stimulates the immobilized microorganism to cause biosynthesis of a specific enzyme system to manifest the activity. However, simple constant supply of the inducer is not sufficient, but the inducer is required to be supplied so as to keep an optimum concentration, because some inducers at a high concentration are harmful to microorganisms to inhibit growth of the cells, and affect adversely the natural environment including humans. For example, a certain Pseudomonas bacterium requires toluene, phenol, or cresol as the inducer for biological decomposition of TCE, with an optimum concentration of the inducer. Naturally an insufficient amount of the inducer does not initiate the activity, while an excessive amount of the inducer inhibits growth of the bacteria. Therefore, the inducer needs to be supplied constantly to keep its optimum concentration for a long period.

However, the introduction of the inducer like phenol and toluene from the outside of the immobilizing carrier is limited since it causes pollution outside the carrier. Because of the low utilization efficiency of the introduced inducer, the amount of the introduction is inevitably larger, which amplifies the pollution. Moreover, the constant supply at the optimum concentration range is extremely difficult. Therefore, use of a bioreactor which employs a microorganism requiring an inducer is restricted greatly. Such problems are not limited to the supply of inducers, but are involved in supply of nutrients and growth factors.

SUMMARY OF THE INVENTION

In view of the aforementioned problems, the present invention intends to provide a carrier for holding an inducer-requiring microorganism with effective utilization of the inducer by the microorganism without secondary pollution by the inducer. The present invention also intends to provide a soil-remedying agent comprising the soil remedying microorganism held on the above carrier, and to provide a method for soil remediation employing the carrier.

The present invention also intends to provide a soil-remedying method which enables optimum supply of water to the microorganism applied to the soil, protection of the applied microorganism from predation by protozoa or the like, and maintenance of the number of the applied microorganism cells and activity of decomposing a polluting substance.

The present invention further intends to provide a soil-remedying method which enables effective diffusion of the microorganism into a polluted region of the soil.

The present invention still further intends to keep a substance like an inducer in the proximity of an immobilized microorganism by a specific constitution without supplying it from the outside of the microorganism-immobilizing carrier, thereby improving the efficiency of utilization of the substance, maintaining the supply thereof at a suitable concentration for a long term, and mitigating the pollution caused by leakage of the substance into the liquid treated by the carrier.

The present invention provides a carrier for holding a microorganism in soil, the carrier releasing, from a constituting material thereof, an inducer for production of an enzyme of the microorganism for soil remediation.

The present invention further provides a carrier for holding a microorganism, comprising a combination of a microorganism holding carrier composed of a hydrophilic polymer for holding the microorganism with an inducer-holder composed of another polymer for holding inducer manifesting a biological action to the microorganism adjacent to each other.

The present invention still further provides a method for remedying soil by application of the above microorganism-holding carrier into the soil.

The present invention still further provide a soil-remedying agent, comprising the above microorganism-holding carrier and a microorganism held thereon which produces an enzyme for decomposition of a polluting substance in the soil by induction caused by an inducer released by the carrier.

BRIEF DESCRIPTION OF THE DRAWINGS

In FIG. 1A, particles of a porous material are attached to particles of a highly water-absorbent polymer. In FIG. 1B, highly water-absorbent polymer particles interpose in the interstices of a porous material. In FIG. 1C, a porous material layer is formed on a highly water-absorbent polymer particle. In FIG. 1D, porous material particles are embedded in a surface layer of a highly water-absorbent polymer particles.

DETAILED DESCRIPTION OF THE PREFERRED EMBODIMENTS

Figure 1A:
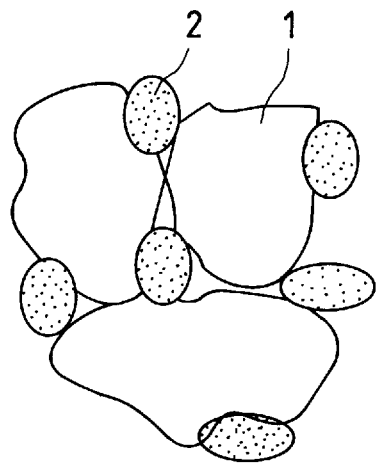
FIGS. 1A to 1D illustrate examples of the structure of the carrier of the present invention.

According to the present invention, soil remediation can be effectively conducted by incorporating or mixing an inducer in a carrier-constituting material, releasing gradually the inducer by degradation or dissolution of the carrier or by elution from the carrier, thus securing survivability of a soil-remedying microorganism by retention of the microorganism in the carrier, and supplying the inducer to the soil-remedying microorganism in the carrier to induce the activity of the enzyme for decomposition of the polluting substance to remedy the soil effectively.

The inducer is selected in accordance with the kind of the soil-remedying microorganism employed. For example, a microorganism which decomposes phenol or methane produces, in the presence of phenol or methane, an enzyme which will decompose it by oxidation. Therefore, production of the enzyme for decomposing phenol or methane is initiated and accelerated for effective decomposition by designing the construction by which phenol or methane is released as an inducer from the carrier. The typical microorganisms capable of decomposing TCE (trichloroethylene) include those requiring an aromatic compound such as phenol and toluene as the inducer; those requiring a hydrocarbon such as methane as the inducer; and those requiring ammonia or an amine as the inducer. Such an inducer interacts with a gene encoding the enzyme production system to cause the gene to express the enzyme. The produced enzyme (e.g., toluene-monooxygenase, methane-monooxygenase, etc.) decomposes the inducer by oxidation, and also is capable of decomposing TCE by oxidation, and therefore decomposes coexisting TCE.

The inducer is usually decomposed or assimilated by the microorganism. However, an excessively large amount of the inducer sometimes inhibits growth of the microorganism. Otherwise, the inducer itself may cause secondary pollution. Accordingly, the carrier is preferably designed to release the inducer at a predetermined concentration or lower from the surface or interior of the carrier.

Inducer substances like phenol exhibit growth inhibiting action or bactericidal action to a variety of bacterial strains. Therefore, the release of such an inducer substance from the surface or interior of the carrier allows selectively survival of bacteria which are resistant to such an inducer substance like phenol. Pseudomonas cepacia KK01 strain, an aerobic bacterium, which is employed in the present invention and capable of assimilating the phenol, can be supported selectively by this carrier and grows therein. Therefore, such bacteria need not be competitive or symbiotic with native microorganisms, and only TCE-decomposing microorganism which is capable of assimilating phenol grows and activated effectively by taking oxygen and nutrients ideally inside the carrier without inhibition.

The material constituting the inducer-containing carrier includes suitably synthetic polymers such as phenol resins, e.g., resol resins, novolak resins, etc., amino resins, e.g., derivatives of melamine and urea, etc., epoxy resins, polyamide resins, polyurethane resins, polyester resins, (meth) acrylic resins, vinyl resins derived from vinyl acetate, vinyl chloride, styrene, etc. and the like; natural polymers such as cellulose and derivative thereof, and the like; and derivatives and mixtures of the above polymers. Of the above polymers, those having high hydrophilicity are suitable for the material for the carrier.

The water-soluble polymer includes:

(a) starches; mannan; polymers of seaweed origin, such agar, and sodium alginate; vegetable polymer such as gum arabia; polymers of microorganism origin such as dextran; and natural polymer such as proteinaceous material, e.g., glue, gelatin, collagen, etc.;

(b) semisynthetic polymers such as cellulose type polymers, e.g., viscose, methylcellulose, ethylcellulose, hydroxycellulose, carboxymethylcellulose, etc.; and starch type polymers, e.g., soluble starch, carboxymethylstarch, dialdehydostarch, etc.;

(c) synthetic polymers such as polyvinyl alcohols, sodium polyacrylate, polyethylene oxide, and the like; and mixtures thereof.

In the case where the hydrophilicity of the employed polymer is not sufficient, preferably a polymer having a higher hydrophilicity or a surfactant is mixed thereto, or a highly polar group such as carboxyl, hydroxyl, amido, and sulfo is introduced to the polymer to raise the hydrophilicity.

Incorporation of the inducer into the carrier-constituting material is conducted by simple mixing with the carrier-constituting material, dispersion as liquid bubbles, incorporation of microcapsule made of the carrier-constituting material, impregnation into or adsorption by a porous material. In mixing the carrier-constituting material with an inducer, the rate of release of the inducer can be controlled by constituting the carrier such that the inducer-containing portions and the biodegradable or water-soluble portions are distributed mixedly.

The biodegradable material includes wood powder and various biological materials, films and foams of bacteria cellulose or cellulose-xanthone composites, bacteria polyesters, polylactic acids, polylactones, polyglyoxylic acids, polymalic acids, starch-added plastics, polycaprolactones, hydroxybutyric acid-hydroxyvaleric acid copolymers, polyaminoacids, polysaccharide polymers, and the like. At least a part of the carrier is constituted from one or more of the above biodegradable material to make the entire carrier or the basic structure of the carrier biodegradable by the microorganism held by the carrier or a soil microorganism.

With such a water-soluble or biodegradable material employed for construction of the carrier, the carrier is dissolved or decomposed at the time when the decomposition of TCE or the like has been completed, or later. With the dissolution or degradation of the carrier, the grown bacteria such as phenol-assimilating bacteria loses its growth environment and decays rapidly, and the ecosystem is restored to the original non-pollution state.

In the case where an excessive substance inhibits growth or exhibits bactericidal action like phenol, the material of the carrier and the releasing mechanism are selected in consideration of the amount and the incorporation state of the substance in construction of the carrier. A gel-state material is preferred since it allows change of the content of the substance like phenol in a broad range and realizes easy control. With such a material sticking to a part of the porous carrier, the present invention can be conducted satisfactorily. The carrier may be a nutrient for the growth of the microorganism incorporated therein. Therefore, the carrier-constituting material preferably is a biological material, or more preferably it contains nutrients mainly constituted of carbon, nitrogen and phosphorous atoms for the microorganism. Incorporation of such a material into the high polymer material or a gel-like material enables acceleration of growth by the nutrients supplied by the carrier.

The carrier has preferably a porous structure or a three-dimensionally crosslinked structure from the standpoint of maintenance of the soil-remedying microorganism. With such a structure, the soil-remedying microorganism in the pores in the carrier is protected from the adverse effects given by other microorganisms in the soil and from predation by protozoa. Thus the growth and the activity of the microorganism are maintained at a satisfactory level, and the microorganism is effectively released in the soil to decompose the polluting substance effectively. When the carrier has a three-dimensional network structure with a suitable size of pores, the polluting substance can be introduced into the carrier to be more effectively decomposed.

The aforementioned three-dimensional network structure has many pores communicating with each other three-dimensionally, and the communication portions of the pores are made relatively large. Therefore, the microorganism and the components can migrate relatively easily. Further, the pores inside the carrier are preferably communicated with the openings on the surface of the carrier, to form through-holes.

The carrier, if it has a porous structure or a three-dimensional network structure, has an average pore diameter preferably in the range of from 1 $\mu$m to 50 $\mu$m, and a pore volume ratio preferably of not less than 50%, more preferably not less than 70%, but not more than 98% to secure the rigidity as the carrier in the soil.

The three-dimensional network structure is obtained, for example, by uniaxial or biaxial stretching, solvent evaporation from a solvent separation film, blending and molding with a filler like silica and subsequent extraction of the filler to form fine pores.

The microorganism is introduced into a carrier in various shapes and containing an inducer, for example, by immersion of the carrier in a liquid culture containing the microorganism, or by separate introduction of the carrier and the microorganism to the application site to introduce the microorganism into the carrier in the site. The effect can be enhanced by supplementing the microorganism or the carrier a certain time after the introduction of the microorganism-holding carrier.

The carrier may be constituted from a highly water-absorbent polymer. The highly water-absorbent polymer is capable of absorbing and holding water in an amount of several ten or several hundred times of the own weight but does not dissolve in water, having highly hydrophilic ionic groups, and having a crosslinked insolubilized structure to prevent dispersion or dissolution of the polymer molecule chain into water.

The highly water-absorbent polymer for constructing the carrier of the present invention has preferably a high gel strength and exhibits preferably high salt resistance in consideration of the use conditions in the soil, and is exemplified by the polymers employed in the fields of agriculture and horticulture. Specific examples include hydrolysis products of starch-acrylonitrile graft copolymers, starch-acrylic acid graft copolymers, starch-styrenesulfonic acid graft copolymers, starch-vinylsulfonic acid graft copolymers, starch-acrylamide graft copolymers, cellulose-acrylonitrile graft copolymers, cellulose-styrenesulfonic acid graft copolymers, crosslinked carboxymethylcellulose, hyaluronic acid, agarose, crosslinked polyvinyl alcohols, crosslinked sodium polyacrylates, sodium acrylate-vinyl alcohol copolymers, saponification products of polyacrylonitrile polymers, and combinations of two or more thereof.

The highly water-absorbent polymer, when used solely, may be in a state of powder, fine powder, pearls, beads, flakes, blocks, etc., and has preferably a diameter in the range of from several hundred $\mu$m to several mm.

The highly water-absorbent polymer may be produced, for example, by polymerizing a hydrophilic monomer (or a hydrophobic monomer modified to be hydrophilic) and crosslinking the resulting polymer, or by crosslinking a polymer obtained by polymerization and modifying the crosslinked polymer to be hydrophilic. The hydrophilicity of the polymer can be achieved by polymerization of a hydrophilic group-containing monomer; introduction of a hydrophilic group to a polymer; graft polymerization of a hydrophilic group-containing monomer onto another polymer; or saponification or hydrolysis of a polymer. The crosslinking or insolubilization of a polymer made from a hydrophilic monomer can be conducted by network-formation with a crosslinking agent; network-formation with a crosslinking monomer; network-formation by self-crosslinking; network-formation by light or radioactive ray irradiation; insolubilization by copolymerization of a hydrophobic monomer; insolubilization by introduction of crystalline polymer blocks; crosslinking by polyvalent metal ions, and so forth.

Figure 1B:
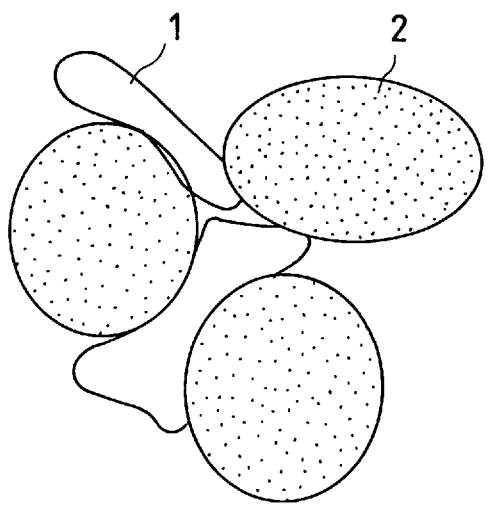
Figure 1C:
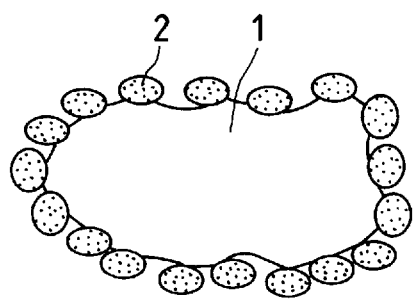
Figure 1D:
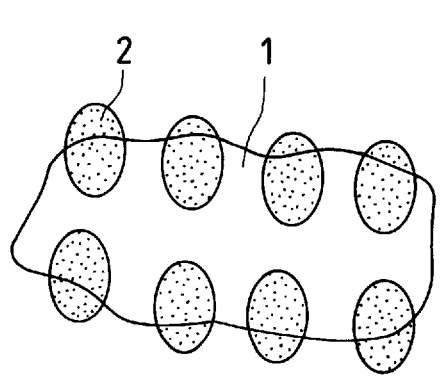

The carrier of the present invention may further contain a porous matter therein for holding a microorganism. Such a porous matter is, for example, preferably capable of forming a "microhabitat" for a microorganism. An example of the structure of the carrier combined with the porous matter is illustrated schematically in FIGS. 1A to 1D. FIGS. 1A and 1B show structures of carriers prepared by mixing and agitating a highly water-absorbent polymer and a porous matter: FIG. 1A showing a structure in which a porous matter particles adhere to highly water-absorbent polymer particles, and FIG. 1B showing a structure in which a highly water-absorbent polymer interposes as a binder in interspace between a porous matter particles to form aggregates. FIG. 1C shows a carrier structure in which a porous matter layer is formed on the surface of a highly water-absorbent polymer particle. FIG. 1D shows a carrier structure in which a porous matter particles are embedded on the surface of a highly water-absorbent polymer particle. Such a carrier can be obtained, for example, by forming a particulate matter from a highly water-absorbent polymer by selecting the conditions of granulation, the kinds and the mixing ratio of the materials of the highly water-absorbent polymer and the porous matter, and so forth. Such a carrier is in a shape mainly of granules or blocks in a size of not less than about 500 μm, at most 2 to 3 cm, and about 1 to 5 mm in average.

The term "microhabitat" means a fine dwelling of the microorganism, and serves to protect the microorganism from severe external conditions. For example, when the outside of the pores becomes extremely dry to adversely affect the growth of the microorganism, the microhabitat retains capillary water therein to supply water to the microorganism. The microhabitat also protects the microorganism from predation by protozoa in the soil. Therefore, the survivability of the microorganism can be raised by artificial formation of the microhabitat in the carrier for the microorganism to be applied and application of this carrier to the soil. Further, the applied microorganism can be dispersed in soil by preparing the carrier in a shape suitable for dispersion in soil.

The porous matter may be used in various shapes such as a granular shape and a laminar shape, and the material therefor includes inorganic materials such as ceramics, glass, calcium silicate, silica, and aggregate-structured soil particles like Kanuma soil; active carbon; organic materials such as urethane foams, anion-exchange resins, cellulose, lignin, chitin, and chitosan; and combinations of two or more thereof. In consideration of large amount of application to soil, the porous matter is desired to be inexpensive.

The porous matter-containing carrier is prepared, for example, by mixing a porous matter holding a desired microorganism with a highly water-absorbent polymer before absorption of water and subsequently allowing an appropriate amount of water or a liquid culture to penetrate the resulting mixture with gentle agitation. Otherwise, the microorganism may be suspended in the water or the liquid culture to be incorporated and allow the liquid mixture to penetrate into the solid mixture. Naturally, the microorganism may be adsorbed firstly to the porous matter and made to adapt to it, and then the porous matter is mixed with the highly water-absorbent polymer in order to increase the amount of the microorganism held on the porous matter. When a mixture of the highly water-absorbent polymer and the porous matter of such a constitution is applied to soil, the porous matter comes into contact with the external soil and the highly water-absorbent polymer is accompanied by it.

If it is required to construct the mixture more precisely than the above, granulation is conducted so that a layer of the porous matter is formed on a part or the entire of the periphery of the highly water-absorbent polymer carrier, or the porous matter particles are embedded to the surface of the highly water-absorbent polymer carrier.

The kind of the porous material is not specially limited. The porous material does not preferably impair migration or dispersion of the carrier in the soil, and is preferably is in a particle shape having a particle diameter in the range of from several hundred μm to several mm. The porous matter has preferably a structure and properties suitable for adsorption or growth of the microorganism; for example, those having pores of from several μm to several ten μm, and those having ion-exchanging groups on the surface to have high ion-adsorption power.

Thus the microorganism, which is held by such a highly water-absorbent polymer with water, can survive, grow, and maintain its decomposition activity without exposure to water-deficient environment, even when the soil to be cleaned contains water at a low content.

Contrary to the soil containing less water, in polluted soil containing water at an extremely high content (e.g., maximum water-holding capacity of 90% or more), the oxygen concentration in the soil is low and the activity of an aerobic decomposition microorganism is extremely low disadvantageously. In such a case, if a highly water-absorbent polymer holding an aerobic decomposition microorganism with no absorbed water is applied to the soil, the highly water-absorbent polymer will absorb excess water to form a gaseous space to improve air permeability, thereby oxygen being supplied to the held microorganism.

To prevent predation of the decomposition microorganism by protozoa, it is effective to remove excess water from the soil while water is supplied to the microorganism held by the highly water-absorbent polymer and to the microorganism released from the polymer by growth. The protozoa migrates in the soil by aid of soil water, the migration depending greatly on the water content of the soil. It is known, for example, typical protozoa, Colpoda, which preys upon bacteria, is limited extremely in migration in the soil of maximum water-holding capacity of 60% or lower to prey little on bacteria, while at the maximum water-holding capacity of 80% or higher, it migrates vigorously and preys actively upon bacteria (Ronald Vargas and Tsutomu Hattori: FEMS Microbiology Ecology, 38 (1986) 233–242).

Therefore, by reducing the content of water utilized for migration of the protozoa in the soil, the migration of the protozoa is restricted, the amount of predation is decreased, and the survivability of the decomposition microorganism is raised.

The highly water-absorbent polymer does not absorb or supplies (gradually releases) water one-sidedly, but it can repeat cycles of absorption and gradual release in accordance with the water content of the soil. Therefore, a polluting substance in a low concentration in soil of low water content, which cannot be decomposed readily, can be decomposed acceleratedly in a following manner. A highly water-absorbent polymer holding a decomposition microorganism without water absorption is applied to polluted soil. To this soil, water or a culture medium is added in consideration of the water content of the soil. The added water or a culture medium into which a small amount of the polluting substance has come to be dissolved is gradually absorbed by the applied highly water-absorbent polymer and thereby is brought close to the decomposition microorganism. At this time, a part of the polluting substance is decomposed by the microorganism. As the water content of the soil, which had once increased by addition of the water or the culture medium, decreases with lapse of time, the absorbed water is gradually released from the highly water-absorbent polymer. In this step also, the polluting substance in the released solution is decomposed by the microorganism. After a certain time when the water content of the highly water-absorbent polymer has decreased, water or the culture medium is again added thereto. Thereby, still remaining small amount of the polluting substance is dissolved in the liquid, and the liquid is absorbed by the highly water-absorbent polymer to decompose the substance by the microorganism in the same manner. By repetition of the steps, the soil containing a polluted substance at a low content and water at a low water content can be cleaned efficiently. This method, in contrast to conventional bioremediation which collects the polluting substance diffused in the soil, is characterized in that a polluting substance is transferred in the soil by utilizing the water absorbing power as the driving force to collect the polluting substance close to the decomposition microorganism. This method makes easy the cleaning of the soil in which a microorganism does not readily diffuse, e.g., soils of a high clay content. The addition of the water or the liquid culture may be conducted in a conventional manner.

The highly water-absorbent polymer is used as an immobilizing carrier in a closed system such as a bioreactor for the purpose of improving the treating capacity of microorganism. In such cases, the microorganism is desirably immobilized such that the microorganism is not released from the carrier, for example, by bridge formation, or entrapment. On the other hand, in the present invention, the highly water-absorbent polymer serves mainly to adjust the water content in the soil environment to maintain the survivability and activity of the microorganism held by the carrier, and grown microorganism released from the highly water-absorbent polymer is expected to diffuse in the soil to come positively into contact with a polluting substance and to decompose the polluting substance. Therefore, the immobilization of the microorganism employed for a closed system is not suitable for the purpose of the present invention. In the present invention, the held microorganism is adsorbed on a surface of a highly water-absorbent polymer or on a surface of a carrier combined with a highly water-absorbent polymer.

The method of the present invention is suitable not only for some kinds of aerobic bacteria, but also for any kind of microorganism, and may be employed for removal of a polluting substance by selecting the microorganism, the highly water-absorbent polymer, and the carrier suitable for the polluting substance to be removed.

The microorganism to be applied may be an already isolated one, or a newly isolated one by screening from natural environment to meet the object, or a mixed system containing two or more kind of microorganism.

A second embodiment of the carrier of the present invention is a combination of a microorganism carrier composed of a hydrophilic polymer for holding a microorganism with an inducer-holder composed of a polymer for holding an inducer. With this combination, the inducer is held in the polymer at a high concentration, and the inducer-containing polymer is placed in contact with the microorganism-holding carrier, whereby the inducer required by the microorganism for the decomposition is gradually supplied by diffusion within the combination, so that the inducer is utilized at an improved utilization efficiency without flowing-out from the carrier; the pollution of the treated liquid is remarkably mitigated; and the compound can be supplied continuously at an appropriate concentration to manifest the intended microorganism activity stably.

In this second embodiment, the hydrophilic polymer for holding the microorganism has a water-retaining ability for giving a biological activity and maintaining survivability of the microorganism, and has a polymeric structure for immobilizing the microorganism by entrapment of lattice type, microcapsule, etc., physical adsorption, bonding such as ionic bonding or covalent bonding, combination of covalent bonding with entrapment. Generally, the hydrophilic polymer is preferably capable of forming hydrophilic gel, such as synthetic polymers derived from acrylic acid, methacrylic acid, styrenesulfonic acid, dimethylaminoethyl methacrylate, 2-hydroxy-3-methacryloxypropyltrimethylammonium chloride, acrylamide, or the like monomers; polysaccharide, e.g., alginic acid, agarose, etc.; polypeptide, e.g., fibrin, collagen, etc.; and derivatives obtained form the mixture of these monomers.

Such a hydrophilic polymer is prepared, for example, by polymerizing a hydrophilic monomer in an aqueous phase and crosslinking the resulting polymer if necessary; or by crosslinking a water-soluble hydrophilic polymer. The resulting polymer encloses an aqueous phase. In the case where the monomer is polymerized by radical polymerization, the polymerization initiator is selected depending on the kind of monomer, the initiator including benzoyl peroxide, azoisobutyronitrile, nitrile peroxide, acetyl peroxide, persulfate salts, and so forth. Photoradical polymerization may be employed by using a photosensitizer such as riboflavin. Also, polysaccharide such as alginic acid may be crosslinked in the presence of calcium ion or magnesium ion into a gelled hydrophilic polymer.

The activity of the microorganism held by such a hydrophilic polymer can be raised and the efficiency of the treatment can be improved by adjusting the ratio of the included aqueous phase, the degree of polymerization, and the degree of crosslinking. The ratio of the aqueous phase included in the hydrophilic polymer is controlled by selecting the monomer concentration, etc. in polymerization. The thickness and the polymerization degree of the constituting polymer can be controlled by addition of a retarder or an inhibitor of polymerization; or stop of light irradiation in photopolymerization.

The kind of the hydrophilic polymer is not specially limited provided that it impairs neither the survivability nor biological activity of the microorganism. The water content of the microorganism-holding carrier is decided in consideration of the working conditions of the carrier and the optimum working conditions of the microorganism, and is preferably in the range of from about 80 to about 95%. The pH of the carrier is adjusted to be in the range of from about 4 to about 9. The amount of the microorganism to be held depends on the kind of the hydrophilic polymer, and is generally in the range of from $10^4$ to $10^9$ cells/ml of the microorganism-holding carrier.

The polymer for holding the inducer in the present invention has a structure allowing migration of the inducer under a certain conditions and not fixing the inducer in an immobile state. The inducer may be either water-soluble or oil-soluble. The hydrophilicity of the polymer is preferably similar to that of the inducer. If the inducer is water-soluble, the inducer-holding polymer is preferably hydrophilic. Thereby, the inducer is movable and diffusible, and can be held by the polymer at a high concentration, which is advantageous in view of the supply to the microorganism in a long term. In this case, the aforementioned hydrophilic material for the microorganism-holding carrier is useful also for holding the inducer. If the inducer is oil-soluble, the inducer-holding polymer is preferably hydrophobic. Thereby, the inducer is diffusible and can be held by the polymer at a high concentration advantageously. The hydrophobic polymer material is exemplified by polystyrene, polyacrylate esters, methacrylate esters, etc.

In the case where the inducer and the inducer-holding polymer are both hydrophilic, no barrier is formed structurally or physicochemically at the boundary between the inducer-holder and the microorganism-holding carrier because the microorganism-holding carrier is hydrophilic. Therefore-the held inducer may diffuse into the microorganism-holding carrier unnecessarily rapidly to be lost. In such a case, a barrier is preferably provided between the microorganism-holding carrier and the adjacent inducer-holder to control the diffusion rate of the inducer. As the diffusion barrier therefor, a hydrophobic membrane such as lipid membranes and polymer membranes may be employed. Otherwise, as the barrier, a polymer membrane layer having a higher crosslinking degree is formed at the interface portion by use of a chemical crosslinking agent.

The lipid for formation of the lipid film includes phospholipids such as phosphatidylcholine, phosphatidylethanolamine, phosphatidylserine, phosphatidic acid, phosphatidylinositol, and phosphatidylglycerol; lysophospholipid corresponding thereto; fatty acids; polymerizable lipids; synthetic surfactant; and so forth. The crosslinking agent for decreasing the diffusion rate of the inducer is selected in consideration of the properties of the polymer to be modified, and includes polylysine, glutaraldehyde, polyethylene glycol, pullulan, N-methylol compounds, dicarboxylic acids, bisepoxides, etc. The lipid layer may be bonded by bridge formation with the hydrophilic polymer of the inducer-holder or the microorganism-holding carrier, if necessary. The bridge formation between the hydrophilic polymer and the lipid membrane stabilizes the membrane structure. The bonding of the lipid membrane with the hydrophilic polymer is conducted by a known bridge formation method, for example, a method employed in chemical modification of protein. For example, for reaction of a carboxyl group with an amino group or a hydroxyl group, a reagent such as carbodiimide is employed which is capable of forming a bridge structure by dehydration-condensation. With such a reagent, a bridge structure is formed between a portion derived from carboxyl group-containing monomer such as acrylic acid, and methacrylic acid and an amphiphilic compound having an amino group such as phosphatidylethanolamine. Similarly a bridge structure is formed between a portion derived from acrylamide and phosphatidylserine. The bridge-formation between an amino group and a thiol group can be conducted with a reagent such as N-succinimidyl-3-(2-pyridyldithio) propionate. By use of such a reagent, for example, a bridge is formed between a peptide polymer and amphiphilic compound having an amino group.

The modification by a chemical crosslinking agent may be conducted such that the crosslinking reaction proceeds from the interface to the interior, thereby the crosslinking degree increasing gradually from the interface to the interior.

In another method for controlling the inducer diffusion rate, the diffusion barrier and/or the inducer-holder is constructed from a functional material which changes its physical, chemical, or structural properties by a factor controllable from the outside. For example, a lipid bimolecular membrane is known to increase its permeability to a low molecular compound around the phase transition temperature, and this property enables the control of gradual release of the inducer by control of the temperature. Similarly, the inducer-holder can be designed such that the gradual release of the inducer may be controlled by changing the holding capacity of the polymer as the inducer-holder by controlling various factors such as temperature, pH, salt concentration, application of electromagnetic field, and so forth. For example, by use of an N-acrylamide type polymer or the like as the polymer, the inducer diffusion rate can be controlled by an external factor such as temperature and pH. In such a manner, a bioreactor can be readily controlled by controlling an external factor to obtain the intended biological activity.

The microorganism-holding carrier and the inducer-holder need to be brought into contact with each other with or without interposition of a diffusion barrier to form a combined body in order to supply the inducer to the microorganism. The type of the combined body is not limited. A larger contact area is preferred for rapid supply of the inducer. Therefore, spherical shape is preferred which has a larger surface area. The inducer-holder may be enclosed in the microorganism-holding carrier, or conversely the microorganism-holding carrier may be enclosed inside the inducer-holder. In the former case, the inducer-holder and the microorganism are commonly enclosed in the same hydrophilic polymer. When the held microorganism is aerobic, the hydrophilic polymer for holding the microorganism is preferably formed as an outermost layer, since dissolved oxygen in the outside liquid needs to reach the microorganism rapidly. The shape of the combined body is not limited to be spherical, but the microorganism-holding carrier and the inducer-holder may be laminated as a film-like structure. The diameter of the inducer-holder is in the range of from 0.1 to 500 $\mu$m. In the embodiment in which the microorganism-holding carrier encloses the inducer-holder, the microorganism-holding carrier has a diameter of from about 1 to about 5000 $\mu$m when it is spherical. When the combined body is in a lamination layer structure, generally the inducer-holder has a thickness of from about 1 $\mu$m to about 5000 $\mu$m, and the microorganism-holding carrier has a thickness of from about 20 $\mu$m to about 5000 $\mu$m. The size is suitably selected in consideration of the object.

In the case where low molecular weight compounds for nutrients for the microorganism other than the inducer such as extracts, sugars, hormones, metal ions, a pH controller are held by the polymer, the low molecular weight compounds may be held together in one polymer, or may be held separately in two or more polymer layers. If the release of the low molecular weight compounds needs to be controlled from the outside, the compounds are preferably incorporated independently in separate polymers. In this case, two or more low molecular weight compounds may be incorporated in one combined body.

The mixing ratio of the microorganism-holding carrier to the inducer-holder is selected in consideration of the amount of the inducer to obtain the intended activity of the microorganism. The amount of the inducer to be held is suitably selected in consideration of relative properties of the inducer and the polymer material.

The process for producing the microorganism-holding carrier of the present invention is described below. In the case where a water-soluble inducer and a hydrophilic polymer for holding thereof are employed, firstly a water-in-oil type emulsion is formed by mixing a water-soluble monomer for hydrophilic polymer formation, a water-soluble inducer, an amphiphilic compound for lipid membrane formation, water, and an organic solvent. In this emulsion, a monomolecular membrane of the amphiphilic compound is oriented on the surface of the water droplets containing the inducer and the water-soluble monomer with the hydrophilic moiety of the amphiphilic compound directed to the water phase inside the droplet and hydrophobic moiety thereof directed to the organic solvent phase (oil phase) outside the droplet. If necessary, a bridge structure is formed between the hydrophilic polymer layer formed in the droplet and the film layer formed from the amphiphilic compound by using the amphiphilic compound linked with the water-soluble monomer. Thereby the monomolecular film of the amphiphilic compound comes to be fixed by bridging with the polymerization of the water-soluble monomer in the droplet. In the resulting inducer-containing particles, the hydrophilic polymer layer is covered with monomolecular film of the amphiphilic compound exhibiting fluidity inversely proportional to the degree of bridging. The polymerization conditions of the water-soluble polymer in the droplet are selected according to the kind of the employed monomer.

The organic solvent for forming the oil phase is hardly water-soluble, including aliphatic hydrocarbons such as hexane, and cyclohexane; aromatic solvents such as benzene, xylene, and toluene; ester type solvents; and so forth. Any hardly water-soluble solvent may be used provided that it allows formation of a monomolecular film of the amphiphilic compound for lipid film formation at the liquid-liquid interface with water.

When the spherical film particles are dispersed in an aqueous solution containing a low-polarity solvent or a surfactant, and thereto the amphiphilic compound is added and the polarity of the solvent is raised or the concentration of the surfactant is lowered, the later added amphiphilic compound molecules adhere to the spherical film particles with the hydrophobic moiety directed to the surface of the spherical film particle to form a bimolecular lipid film layer on the surface. The amphiphilic compound added later to the aqueous phase containing dispersed spherical film particles is in a form of a reversed micelle when a low-polar solvent is used, or in a form of a micelle of the same surfactant when a surfactant is used. The method for raising the polarity of the solvent is exemplified by reversed phase evaporation. The method for lowering the concentration of the surfactant is exemplified by dilution, dialysis, and gel filtration. The amount of the later added amphiphilic compound is to be sufficient for formation of the bimolecular lipid film, and an excess amount of addition is to be avoided not to form unintended liposome or undesired multimolecular-layer lipid film. If unintended liposome is formed, it can be removed by density-gradient centrifugal fractionation, gel filtration, and the like method. An oil-soluble low-molecular compound can be supported by the bimolecular lipid film layer by forming the bimolecular lipid film in the presence of the desired oil-soluble low-molecular compound. The composition of the internal layer and the external layer of the bimolecular film of the lipid layer may be different. Further, the later added amphiphilic compound may be the one which is capable of forming a bridge with a monomer for further formation of a hydrophilic polymer layer on the lipid film layer.

The method of further lamination of a hydrophilic microorganism-holding polymer layer on the surface of spherical film particles having the above bimolecular lipid film layer is described below. The second hydrophilic polymer layer can be produced on the basis of the same principle as the formation of the inducer-holder. Specifically, a spherical combined matter which contains the microorganism-holding carrier containing therein the inducer-holder and the microorganism can be prepared by adding, according to the aforementioned method, the spherical inducer-holder and the microorganism in place of the inducer. In another method, a polymerization initiator, a photopolymerization sensitizer, or the like is enclosed in the spherical inducer-holder (spherical film particles), the spherical inducer holder is dispersed in a medium containing a water-soluble monomer for hydrophilic polymer layer formation for holding the microorganism, allowing the enclosed polymerization initiator or the photopolymerization sensitizer to leak out of the spherical film particles, and if necessary, light is applied to cause isotropic polymerization around the spherical film particles.

The enclosure of the polymerization initiator, etc. in the spherical film particles and the leakage thereof can be conducted by utilizing phase transfer of the lipid film layer caused by temperature conditions. Permeability of a low-molecular weight substance in a bimolecular lipid film becomes maximum at about the phase transition temperature. Therefore, when the spherical film particles are dispersed in a solution of the polymerization initiation reagent and the dispersion is brought to the phase transition temperature, the reagent can penetrate into the spherical film particles. When the penetration of the reagent is completed, the reagent can be enclosed in the spherical film particles by changing the temperature of the spherical film particles to exhibit low or no permeability. The reagent can be allowed to leak out from the spherical film particles by recovering the film permeability by bringing the temperature of the spherical film particles approximately to the phase transition temperature.

The thickness of the hydrophilic polymer layer on the lipid film layer can be controlled by stopping the polymerization. The stop of the polymerization is conducted by stop of light irradiation, addition of a polymerization inhibitor, or the like procedure. The microorganism can be incorporated into the hydrophilic polymer layer by adding the microorganism to the water-soluble monomer. When the outer layer of the lipid film layer has a bridge structure with water-soluble monomer for hydrophilic polymer formation, a bridge structure can be obtained between the lipid film layer and the hydrophilic polymer layer.

The method for forming lamination of an inducer-holder and a microorganism-holding carrier in film state is described below. For this method, a substrate is used for lamination of the films. The substrate is selected in consideration of the use of the film structure. For example, to impart a physical strength to the film structure, substrates are used which are made of inorganic materials and polymer materials including of glass, mica, and plastics such as polyphosphonitrile chloride; and fibers. To utilize electric properties, the substrate includes base plates made of electroconductive or semiconductive material such as a metal and graphite; chemically modified electrodes, polymer-coated electrodes, etc.

Since the hydrophilicity (or the hydrophobicity) of the substrate surface affects the lamination constitution, surface properties of the substrate is controlled to meet the object. For example, on a hydrophilic substrate surface, the lipid film layer formed thereon has its hydrophilic polymer layer or hydrophilic moieties oriented to the substrate surface side, whereas on a hydrophobic substrate surface, a lipid film layer formed thereon has its hydrophobic moieties oriented to the substrate surface side.

The procedure for forming the film structure is basically the same as that of the spherical structure. For example, firstly, a monomer for hydrophilic polymer layer formation containing a water-soluble inducer is polymerized on a substrate. This substrate having the hydrophilic polymer layer is immersed in an organic solvent containing an amphiphilic compound for lipid film layer formation. Thereby, on the upper face of the hydrophilic polymer layer on the substrate, a monomolecular layer of the amphiphilic compound is formed with its hydrophilic moieties oriented to the hydrophilic polymer surface side. If the amphiphilic compound contains moieties capable of forming bridges with the formed hydrophilic polymer layer, a bridge structure formed between the hydrophilic polymer layer and the lipid film layer. In the same manner, a further lipid monomolecular film, and a microorganism-holding layer are repeatedly formed to obtain a desired multi-layered structure.

In the case where an oil-soluble inducer is employed, the holding carrier is obtained by changing the polarity of the materials based on the same principle as above. When a hydrophobic polymer is used as the inducer-holder, diffusion barrier such as a lipid film layer need not be provided at the interface with the microorganism-holding carrier, and the bonding with the hydrophilic polymer of the microorganism-holding carrier can be formed based on the same principle as above.

The carrier itself of the present invention applied to the soil gives native microorganisms a place for proliferating, and leaves the inducer to dissolve by release of the inducer from the carrier surface or by collapse of a portion of the carrier itself by dissolution or biodegradation to induce intentionally production of an enzyme required for the decomposition of a polluting substance to remedy the soil.

Otherwise, a microorganism for soil remediation is held on a carrier and is applied to soil to remedy the soil as desired.

EXAMPLE 1

(1) Incubation of Pseudomonas cepacia KKO1 (Hereinafter Referred to as KKO1 Strain):

To 100 ml of a culture composed of M9 medium supplemented with 0.05% yeast extract (the composition of M9 medium below), was inoculated a phenol-decomposing bacteria, Pseudomonas cepacia KKO1 (Deposit No. FERM BP-4235, Deposition Date: May 11, 1992, deposited to Biotechnology Research Institute of Agency of Industrial Science and Technology, MITI under Budapest Treaty), and was incubated at 30° C. to obtain O.D. (660 nm) of about 0.7.

M9 medium composition (per liter):
$Na_2HPO_4$: 6.2 g
$KH_2PO_4$: 3.0 g
NaCl: 0.5 g
$NH_4Cl$: 1.0 g (2) Preparation of Porous Phenol Resin Carrier With 100 parts by weight of a resol type phenol resin (trade name: PR-HR-40, manufactured by Sumitomo Bakelite Co., Ltd.), were mixed 10 parts by weight of aqueous 10% solution of a nonion surfactant (polyoxyethylene nonylphenol ether, moles of added ethylene oxide: about 50), 5 parts by weight of acetone, and 10 parts by weight of ammonium carbonate. To the resulting mixture, 5 parts by weight of quick lime was added and stirred. Immediately thereafter, 10 parts by weight of 30% hydrochloric acid was mixed therewith, and the mixture was left standing to obtain a porous phenol resin. The resulting porous phenol resin was pulverized, and then dried in vacuum to obtain a carrier having an average particle diameter of 500 $\mu$m.

(3) Inoculation of Bacteria on Carrier

The carrier made of the above porous phenol resin was immersed in a 10% aqueous phenol solution, and dried. The dried carrier was immersed in the KKO1 liquid culture prepared in the above Item (1) to introduce the bacteria by adsorption on the surface and in the pores of the carrier.

(4) Remediation of Soil

Figure 2:
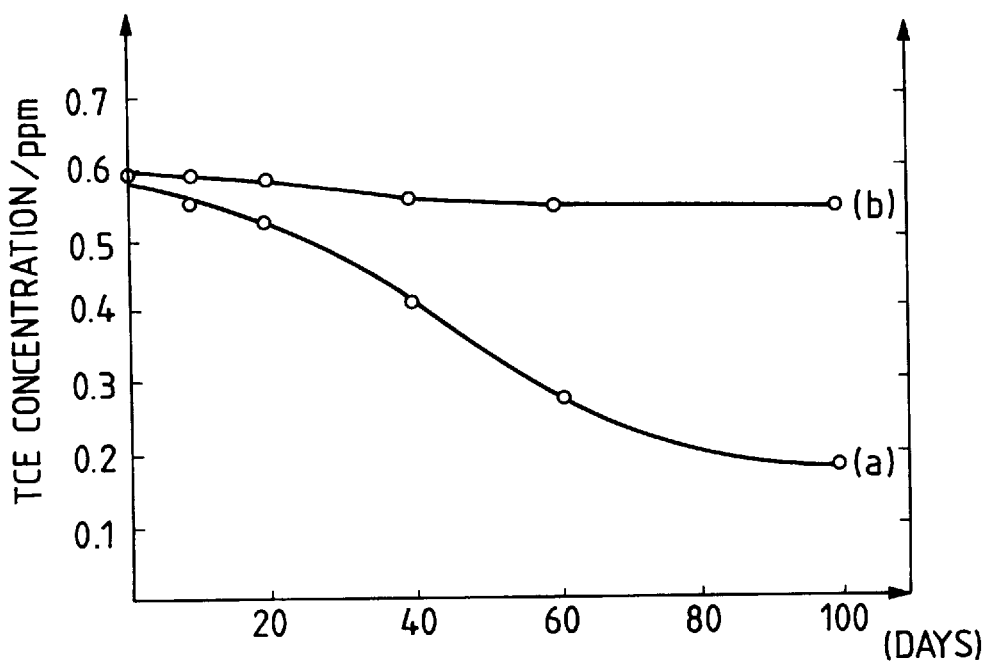
FIG. 2 is a graph showing change of TCE concentration in soil in Example 1 and Comparative Example 1: the curve (a) showing the change of TCE concentration in Example 1, and the curve (b) showing the change of TCE concentration in Comparative Example 1.

Kanto loam soil was taken from natural forest at a depth of about 1 meter. The soil was a uniform mixture composed of gravel (about 10%, the diameter of soil particle larger than 2 mm), sand (about 40%, 75 $\mu$m to 2 mm), silt (about 30%, 5 $\mu$m to 75 $\mu$m), and clay (about 20%, smaller than 5 $\mu$m). The soil was adjusted to have a water content ratio of 90%, and TCE was mixed to the soil at a concentration of 0.6 ppm (by weight of dry soil). This soil was filled in a tightly closable container of 50 cm in diameter and 70 cm in depth. 500 Grams of the above bacterium-inoculated carrier was mixed uniformly to the soil, and the container was tightly closed, and placed in a thermostatic chamber at 25° C. The change of the TCE concentration was monitored by sampling of the soil and extraction with hexane. FIG. 2, curve (a) shows the change of the TCE concentration.

Comparative Example 1

Experiment was conducted in the same manner as in Example 1 except that phenol was not incorporated into the phenol resin. FIG. 2, curve (b) shows the change of the TCE concentration.

EXAMPLE 2

To 10 parts by weight of a porous cellulose particle carrier having an average particle diameter of about 200 $\mu$m (Microcarrier, manufactured by Asahi Chemical Co., Ltd.), was added 100 parts by weight of aqueous 1% phenol solution. The mixture was stirred under reduced pressure to deaerate it. The cellulose particles were separated and dried. Then the cellulose was immersed into the KKO1 liquid culture to introduce the bacteria onto the surface and internal pores of the carrier by adsorption to obtain a bacterium-inoculated carrier.

Figure 3:
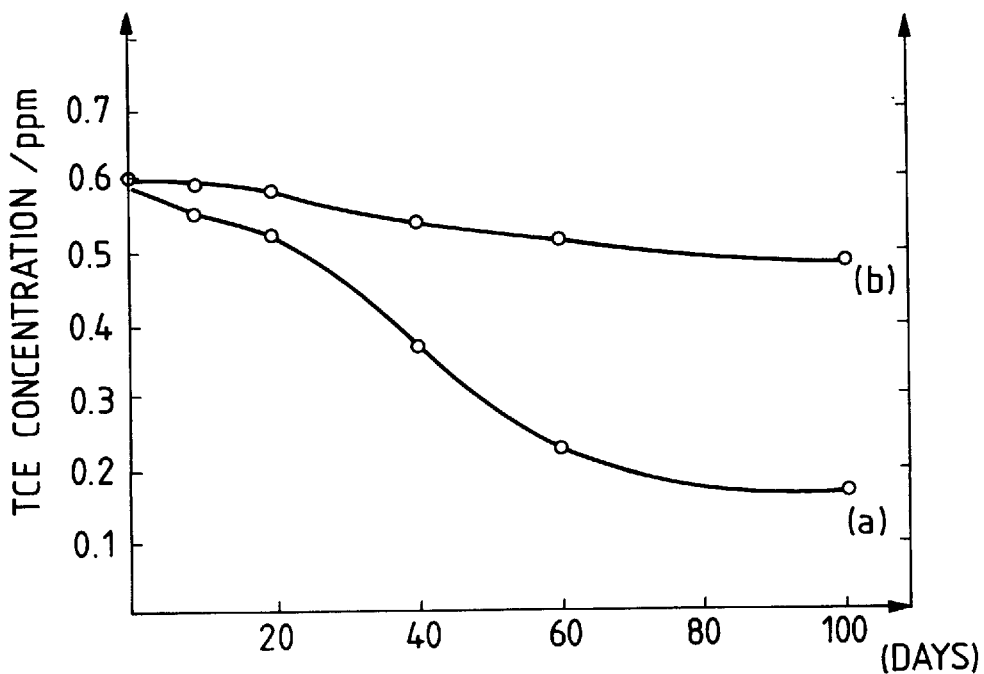
FIG. 3 is a graph showing change of TCE concentration in soil in Example 2 and Comparative Example 2: the curve (a) showing the change of TCE concentration in Example 2, and the curve (b) showing the change of TCE concentration in Comparative Example 2.

200 Grams of this bacterium-inoculated carrier was mixed uniformly with the polluted soil prepared similarly as in Example 1, and the change of TCE concentration was monitored in the same manner as in Example 1. FIG. 3, curve (a) shows the result.

Comparative Example 2

The experiment was conducted in the same manner as in Example 2 except that phenol was not incorporated into the porous cellulose particle carrier. FIG. 3, curve (b) shows the result.

EXAMPLE 3

Figure 4:
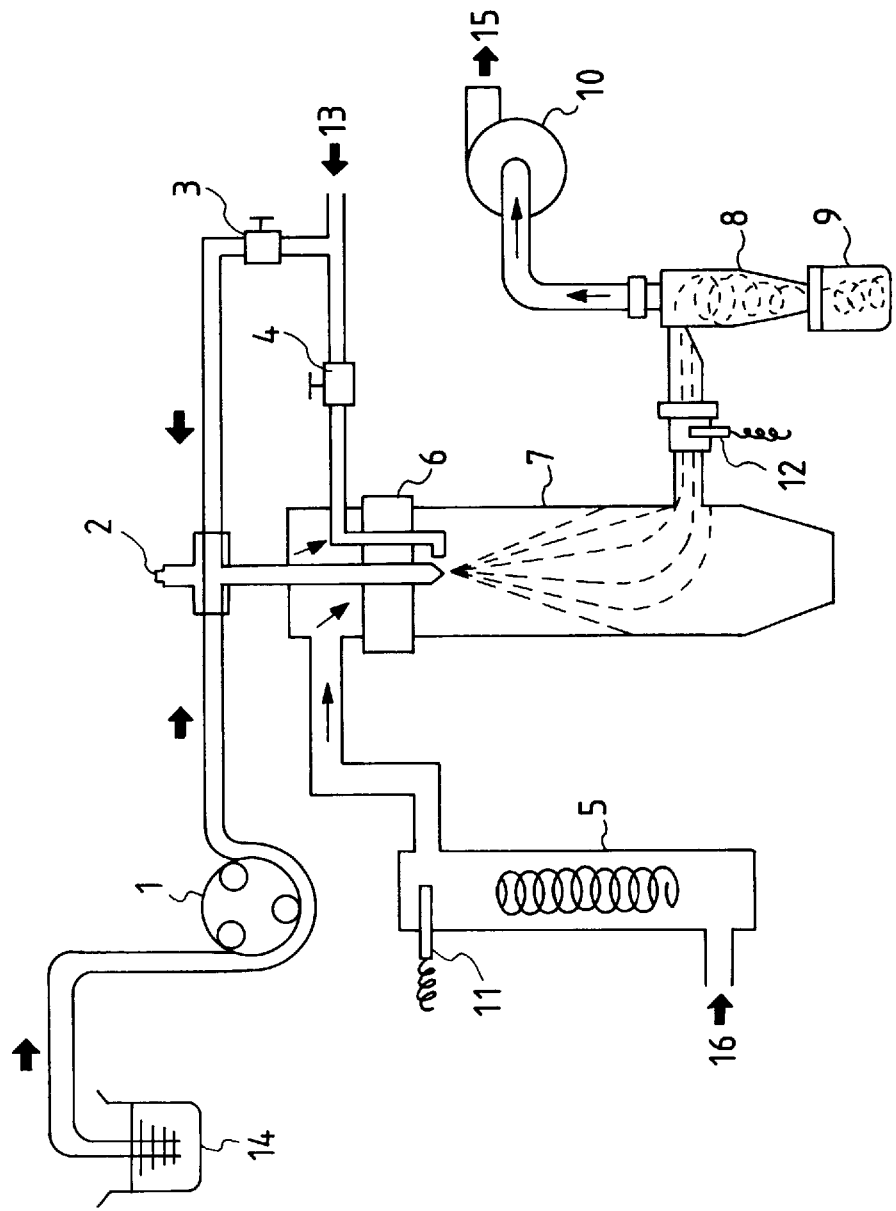
FIG. 4 illustrates roughly the granulation apparatus employed in Example 3.

With 100 parts by weight of the KKO1 liquid culture prepared in the same manner as in Example 1, were mixed 100 parts by weight of an aqueous 10% solution of a hydroxyl-modified acrylic resin solution (ethyl acrylate/hydroxyethyl acrylate/methacrylic acid copolymer), 1 part by weight of a methylated methylolmelamine, 1 part by weight of p-toluenesulfonic acid, and 0.1 part by weight of phenol. The resulting liquid mixture was treated for granulation and drying with the Barubini Mini-Sprayer (Model GA-32, manufactured by Yamato Kagaku K.K.) shown in FIG. 4 at an inlet temperature of 140° C. and an outlet temperature of 40° C. to obtain a bacterium-inoculated carrier. In the figure, each number means as follows: 1:pump; 2:atomizing nozzle; 3:needle valve; 4:electromagnetic valve; 5:heater; 6:distributor; 7:drying chamber; 8:cyclone; 9:vessel for product; 10:aspirator; 11:entrance sensor; 12:exit sensor; 13:pressure air; 14:mixed solution; 15:exhaust; and 16:intake.

Figure 5:
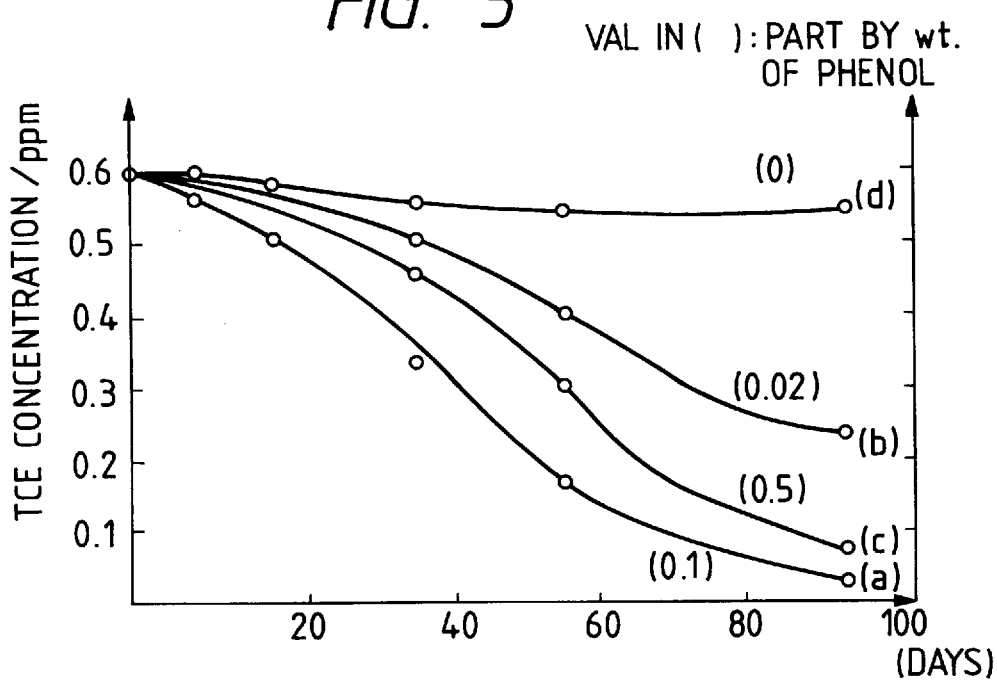
FIG. 5 is a graph showing change of TCE concentration in soil in Examples 3 and 4 and Comparative Example 3: the curves (a) to (c) showing the change of TCE concentration in Examples 3 and 4, and the curve (d) showing the change of TCE concentration in Comparative Example 3.

500 Grams of this bacterium-inoculated carrier was mixed uniformly with the TCE-polluted soil prepared similarly as in Example 1, and the change of TCE concentration was monitored in the same manner as in Example 1. FIG. 5, curve (a) shows the result.

EXAMPLE 4

The experiments were conducted in the same manner as in Example 3 except that the amount of the phenol added to the carrier was changed to 0.02 part by weight or 0.5 part by weight. FIG. 5, curves (b) and (c) show the results.

Comparative Example 3

The experiment was conducted in the same manner as in Example 3 except that phenol was not added to the carrier. FIG. 5, curve (d) shows the result.

EXAMPLE 5

(Effects of highly water-absorbent polymer on TCE-decomposing property of Pseudomonas cepacia KKO1 strain)

KKO1 strain was inoculated in 100 ml of culture (M9 medium with 0.05% yeast extract) and was incubated at 30°

C. to attain O.D.(660 nm) of 0.7. Thereto 10 ml of M9 culture containing 200 ppm of phenol was added. The mixture was further mixed with 100 mg of a highly water-absorbent crosslinked polyacrylic acid (Sun Wet IM-5000D, produced by Sanyo Chemical Co., Ltd.) by stirring gently with a stirrer (PR-300, manufactured by Fujiware Seisakusho K.K.) at 300 rpm to obtain a highly absorbent polymer carrier. The obtained carrier has a structure as shown in FIG. 1A with the particle diameter of the highly water-absorbent polymer of from 3 mm to 4 mm.

This highly water-absorbent polymer carrier was mixed with 50 g of unsterilized brown forest soil of water content ratio of 50% and containing 1 mg of TCE in a 100-ml flask, and then the flask was closed tightly with a silicone stopper. Fifteen samples were prepared in the same manner as above, and were kept standing in a thermostated incubator at 30° C.

Figure 6:
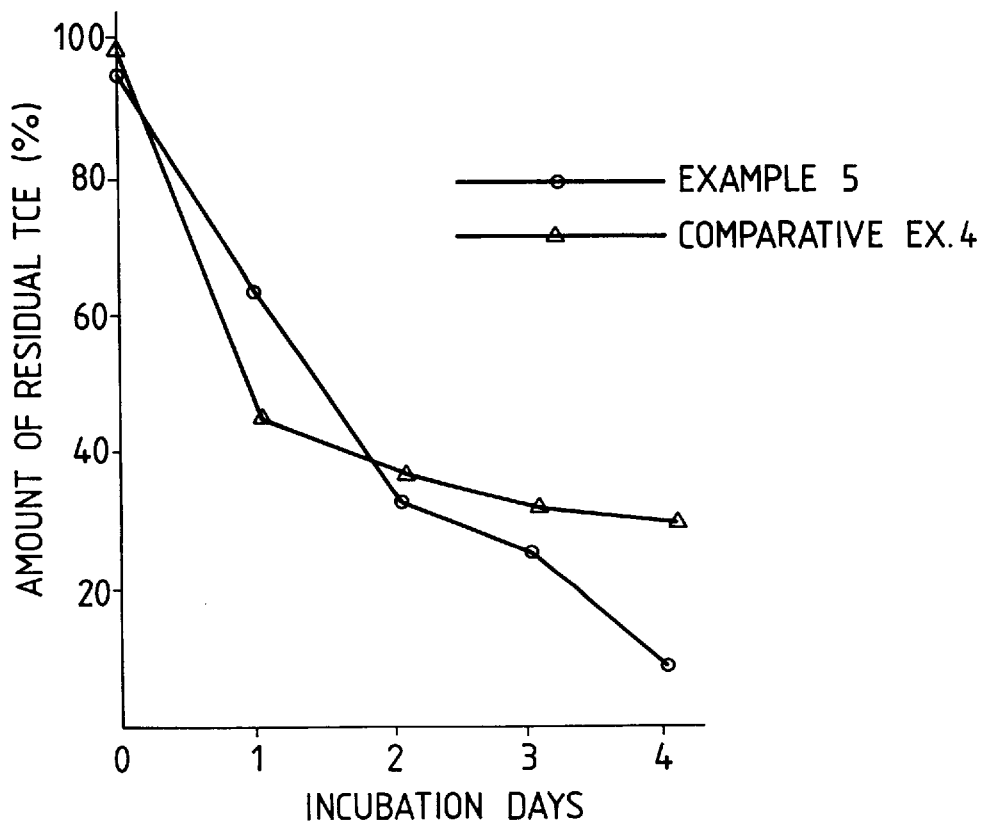
FIG. 6 is a graph showing the change of bacteria cell numbers in the test soil in Example 5 and Comparative Example 5.

The TCE concentrations in the headspace gas phase of the respective flasks were determined at the start of the incubation, and one day, two days, three days, and four days thereafter by gas chromatography. The experiment was conducted in three runs, and the average value was calculated. FIG. 6 shows the results.

Comparative Example 4

To 10 ml of the P. cepacia KKO1 strain incubated in the same manner as in Example 5, was added 10 ml of M9 medium containing 200 ppm of phenol. The mixture was further mixed with the same soil as in Example 5, and the soil was placed in vials, and incubated at 30° C. The TCE concentrations in the headspace gas phase of the respective vials were determined at the start of the incubation, and one day, two days, three days, and four days thereafter by gas chromatography. The experiment was conducted in three runs, and the average value was calculated. FIG. 6 shows the results.

EXAMPLE 6

In this Example, were employed Pseudomonas cepacia KKO1 strain (FERM BP-4235) having TCE decomposition activity as the microorganism, phenol as the water-soluble inducer of biological-activity, and a polyacrylamide gel as the carrier and holder of the above microorganism and the inducer. The spherical microorganism-holding carrier coated with a bimolecular lipid film was used as the inducer-holder.

(1) Preparation of phenol-holding acrylamide gel

The solutions (a) and (b) below were prepared.

(a) Aqueous solution A: 50 mM Tris hydrochloric acid buffer solution containing 10% acrylamide, 0.27% N,N'-methylenebisacrylamide, and 17 mg/ml ammonium persulfate (pH: 8.0).

(b) Lipid solution B: a solution of lipid in chloroform at a concentration of 25 mg/ml, where the lipid is a mixture composed of saturated-type phosphatidylcholine as the main component, and phosphatidylethanol amine and cholesterol. The gel/liquid crystal phase transfer temperature (Tc) was about 45° C.

108 Milliliters of a toluene-chloroform mixed solvent (volume ratio, 7:3) was placed under nitrogen stream in a 300-ml four-neck flask provided with a nitrogen-introducing inlet, a thermometer, a septum stopper for liquid injection, and a blade type stirrer. 12 Milliliters of the aqueous solution A to which phenol had been added to a concentration of 1000 ppm was added to the flask. Having been stoppered closely with the septum, the content of the flask was stirred at 1000 rpm on an ice bath. By use of an injection tube, 1.5 ml of the lipid solution B was injected gradually through the septum stopper into the flask. With the injection of the lipid, the content of the flask came to be emulsified and become white turbid. Further, 300 μl of N,N,N',N'-tetramethylethylenediamine was taken with a microsyringe and was injected through the septum stopper into the flask. Within 10 minutes, heat was generated, and thereafter the content in the flask was stirred for one hour. Then 100 ml of toluene was added to lower the specific gravity of the organic layer. A glass centrifugation tube was filled with a half volume of water, and thereon the organic solvent phase was transferred. Centrifugation was conducted at 3000 ppm for 15 minutes. The organic solvent phase became clear, and formed polyacrylamide gel particles containing phenol was transferred to the aqueous phase and precipitated. The average diameter of the gel particles was found to be 40 μm by optical microscopy. From quantitative determination of the lipid, the surface of the gel particles was found to be coated with a bimolecular film of a phospholipid.

(2) Entrapping immobilization of microorganism in phenol-holding particles

The KKO1 strain was inoculated into 50 ml of culture (M9 medium containing 5 ppm of TCE and 0.05% yeast extract, and 100 ppm of phenol), and was incubated at 30° C. for 2 days. The obtained bacterial mass (wet weight: 100 mg) was suspended in 12 ml of the above water solution A. Thereto, the phenol-containing gel particles prepared in the above item (1) was added in an amount of ¼ by wet volume.

108 Milliliters of a toluene-chloroform mixed solvent (volume ratio, 7:3) was placed under nitrogen stream in a 300-ml four-neck flask provided with a nitrogen-introducing inlet, a thermometer, a septum stopper for liquid injection, and a blade type stirrer. 12 Milliliters of above-mentioned mixture of the gel particles and the bacterial mass was added to the flask. Having been stoppered closely with the septum, the content of the flask was stirred at 500 rpm on an ice bath. By use of an injection tube, 1.5 ml of the lipid solution B was injected gradually through the septum stopper into the flask. Further, 300 μl of N,N,N',N'-tetramethylethylenediamine was taken with a microsyringe and was injected through the septum stopper into the flask. Within 10 minutes, heat was generated, and thereafter the content in the flask was stirred for 20 minutes. Then by the same centrifugation operation as in the above item (1), the particles holding the bacterial mass was transferred to the aqueous phase and was recovered. By optical microscopical observation, the biomass-holding particles was found to have an average particle diameter of 100 μm, and the polyacrylamide gel particles are confirmed to hold the polyacrylamide gel particles prepared in the above item 1 as well as the KKO1 strain.

(3) Decomposition of TCE

Preparation of soil

Kanto loam soil was taken from natural forest at a depth of about 1 meter. The soil was a uniform mixture composed of gravel (about 10%, larger than 2 mm), sand (about 40%, 75 μm to 2 mm), silt (about 30%, 5 μm to 75 μm), and clay (about 20%, smaller than 5 μm). The soil was adjusted to have a water content ratio of 90%, and TCE was mixed to the soil at a concentration of 5 ppm (by weight of dry soil). This soil was filled in a tightly closable container of 5 cm in diameter and 10 cm in depth.

Decomposition of TCE

5 Grams of the above KKO1 strain-holding carrier was mixed uniformly to the above soil. The change of the TCE concentration in the soil at 25° C. was monitored by hexane extraction and ECD gas chromatography. As the results, the TCE concentration was found to fall to less than half level 40 days after start of the experiment, and to 0.08 ppm in 120 days, which shows that the decomposition by TCE decomposition bacteria is effectively accelerated. Elution of phenol was hardly detectable (less than 0.1 ppm).

According to the present invention, the cell numbers of an applied microorganism in soil can be maintained by holding the microorganism on a carrier, and the migration ability and dispersion ability of the applied microorganism can be maintained.

When microorganism-holding carrier is constructed such that a polymer holding an inducer capable of exhibiting biological action to a microorganism at a high concentration is brought adjacent to a microorganism-holding carrier, the inducer necessary for growth of the microorganism is supplied gradually to the microorganism by diffusion in the combined matter of the carrier and the polymer. Thereby, loss by elution of the inducer to the outside is prevented to improve the utilization efficiency of the inducer, and contamination of the treated liquid is mitigated remarkably. Further, the inducer can be supplied continuously at a suitable concentration to keep stable the intended microbiological activity.

When the hydrophilicity of the inducer is similar to that of the holder for holding the inducer, the concentration of the inducer in the inducer holder can be raised, thereby enabling acceleration of diffusion to heighten the intended microbiological activity.

When the inducer and the inducer-holing polymer are hydrophilic, the inducer tends to diffuse and be lost through the microorganism-holding polymer which is hydrophilic. However, by interposing a diffusion barrier between the microorganism carrier and the inducer-holder, the release of the inducer can be controlled to be more gradual, thereby the inducer being supplied to the microorganism stably for a long term. With the diffusion barrier made of a functional film such as lipid film, in particular, a bimolecular lipid film, the gradual release of the inducer can be controlled by temperature, whereby the intended activity of the microorganism can readily be controlled.

By incorporating a spherical inducer-holder in a spherical microorganism-holding carrier, pollution caused by leakage of the inducer is more effectively lowered, the microorganism can be activated more effectively by increasing the contact area. Additionally, spherical structure of the carrier particles increases the treatment area to raise the efficiency of treatment.

What is claimed is:

1. An agent for remedying a soil contaminated with a pollutant
    containing a carrier, wherein the carrier comprises a highly water-absorbent polymer holding a microorganism capable of degrading the pollutant in the presence of an inducer and an inducer capable of causing the microorganism to express an enzyme to degrade the pollutant.

2. The agent according to claim 1, wherein the pollutant is a chlorinated aliphatic compound.

3. The agent according to claim 2, wherein the pollutant is trichloroethylene.

4. The agent according to claim 1, wherein the microorganism expresses oxygenase in the presence of the inducer.

5. The agent according to claim 1, wherein the highly water-absorbent polymer is a polymer capable of absorbing and retaining water in an amount from several ten to several hundred times its own weight.

6. The agent according to claim 1, wherein the highly water-absorbent polymer is a polymer selected from the group consisting of hydrolysis products of starch-acrylonitrile graft copolymers, starch-acrylic acid graft copolymers, starch-styrenesulfonic acid graft copolymers, starch-vinylsulfonic acid graft copolymers, starch-acrylamide graft copolymers, cellulose-acrylonitrile graft copolymers, cellulose-styrenesulfonic acid graft copolymers, crosslinked carboxymethylcellulose, hyaluronic acid, agarose, crosslinked polyvinyl alcohols, crosslinked sodium polyacrylates, sodium acrylate-vinyl alcohol polymers and saponification products of polyacrylonitrile polymers.

7. The agent according to claim 1, wherein the carrier further comprises porous particles.

8. The agent according to claim 7, wherein the porous particles are attached to the highly water-absorbent polymer.

9. The agent according to claim 7, wherein the porous matter particles are embedded in the highly water-absorbent polymer.

10. The agent according to claim 7, wherein the highly water-absorbent polymer has a particle form and the porous particles are on the surface of the highly water-absorbent polymer particle.

11. An agent for remedying a soil contaminated with a pollutant containing a carrier holding a microorganism capable of degrading the pollutant in the presence of an inducer and an inducer capable of inducing the microorganism to express an enzyme to degrade the pollutant, wherein the inducer is surrounded by a barrier film permeable to the inducer, and wherein the carrier and inducer are in contact with each other.

12. The agent according to claim 11, wherein the barrier film is capable of controlling releasability of the inducer.

13. The agent according to claim 12, wherein the barrier film is surrounded by hydrophilic polymer fixing the microorganism, the hydrophilic polymer being an outermost layer of the carrier.

14. The agent according to claim 12, wherein the barrier film comprises a lipid film.

15. The agent according to claim 11, wherein the carrier comprises a hydrophilic polymer in which the microorganism is held, and the inducer surrounded by the barrier film is contained in the hydrophilic polymer.

16. The agent according to claim 15, wherein the hydrophilic polymer is a highly water-absorbent polymer.

17. The agent according to claim 11, wherein the microorganism is *Pseudomonas cepacia* KKO1 and the inducer is phenol.

18. The agent according to claim 11, wherein the inducer is contained in a polymer having a structure allowing migration of the inducer, and the polymer is surrounded by the barrier film.

19. A method for remedying a soil contaminated with pollutant comprising:
    administering into a pollutant-contaminated soil an agent comprising a carrier containing a microorganism capable of degrading the pollutant in the presence of an inducer and a highly water-absorbent polymer containing an inducer capable of causing the microorganism to express an enzyme to degrade the pollutant.

20. A method for remedying a soil contaminated with pollutant comprising:
    administering into a pollutant-contaminated soil an agent comprising a carrier containing a microorganism capable of degrading the pollutant in the presence of an inducer and an inducer capable of inducing the microorganism to express an enzyme to degrade the pollutant, the inducer being surrounded by a barrier film permeable to the inducer.

21. An agent for remedying a soil polluted with a pollutant containing
   a carrier which comprises a microorganism and an inducer, the microorganism capable of degrading the pollutant in the presence of the inducer and the inducer capable of inducing the microorganism to express an enzyme for degrading the pollutant, wherein the inducer is a compound selected from the group consisting of phenol, toluene and cresol.

22. The agent according to claim 21, wherein the microorganism is Pseudomonas cepacia KKO1.

23. A method for remedying a soil contaminated with a pollutant comprising the steps of:
   administering into a pollutant-containing soil, an agent containing a carrier which comprises a microorganism and an inducer, the microorganism capable of degrading the pollutant in the presence of an inducer and the inducer capable of inducing the microorganism to express an enzyme for degrading the pollutant, wherein the inducer is a compound selected from the group consisting of phenol, toluene and cresol.

24. The method according to claim 23, wherein the microorganism is *Pseudomonas cepacia* KKO1.

25. A method for remedying a soil contaminated with pollutant comprising:
   administering to the soil a carrier comprising a highly water-absorbent polymer containing an inducer to induce a microorganism present in the soil and capable of expressing an enzyme for degrading the pollutant, to express the enzyme; and degrading the pollutant by the microorganism.

* * * * *

UNITED STATES PATENT AND TRADEMARK OFFICE
CERTIFICATE OF CORRECTION

PATENT NO. : 5,863,789

DATED : January 26, 1999

INVENTOR(S) : TOSHIYUKI KOMATSU, ET AL.   Page 1 of 3

It is certified that error appears in the above-identified patent and that said Letters Patent is hereby corrected as shown below:

Title page,
AT [56] REFERENCES CITED

OTHER PUBLICATIONS

In French et al., "Degration" should read --Degradation--;
    In Odelson, et al., "nutrition" should read --Nutrition--; and
    In Asahi Chem, "55066501" should read --55-066501--.

Title page,
AT [57] ABSTRACT

Line 14, "action" should read --the action--.

COLUMN 1

Line 19, "microorganism-mobilizing" should read --microorganism-immobilizing--;
    Line 52, close up right margin;
    Line 53, close up left margin; and
    Line 58, "ism" should read --isms--.

COLUMN 2

Line 34, "microorganism" should read --microorganisms--.

COLUMN 4

Line 54, "provide" should read --provides--.

COLUMN 6

Line 10, "activated" should read --is activated--; and
    Line 25, "such" should read --such as--.

UNITED STATES PATENT AND TRADEMARK OFFICE
CERTIFICATE OF CORRECTION

PATENT NO. : 5,863,789

DATED : January 26, 1999

INVENTOR(S) : TOSHIYUKI KOMATSU, ET AL.

It is certified that error appears in the above-identified patent and that said Letters Patent is hereby corrected as shown below:

COLUMN 9

Line 51, "and is" should read --and--.

COLUMN 10

Line 28, "supplies (gradually releases)" should read --supply (gradually release)--.

COLUMN 12

Line 34, "a" should be deleted; and
    Line 55, "Therefore-the" should read --Therefore the--.

COLUMN 16

Line 26, "of" should be deleted; and
    Line 34, "is" should read --are--.

COLUMN 17

Line 27, "Carrier" should read --Carrier:--;
    Line 31, "nonion" should read --nonionic--;
    Line 41, "Carrier" should read --Carrier:--; and
    Line 47, "Soil" should read --Soil:--.

COLUMN 19

Line 45, "gel" should read --gel:--.

UNITED STATES PATENT AND TRADEMARK OFFICE
CERTIFICATE OF CORRECTION

PATENT NO. : 5,863,789

DATED : January 26, 1999

INVENTOR(S) : TOSHIYUKI KOMATSU, ET AL.

It is certified that error appears in the above-identified patent and that said Letters Patent is hereby corrected as shown below:

COLUMN 20

Line 13, "was" should read --were--;
   Line 20, "particles" should read --particles:--;
   Line 27, "was" should read --were--;
   Line 44, "was" (both occurrences) should read --were--;
   Line 46, "was" should read --were--; and
   Line 50, "TCE" should read --TCE:--.

COLUMN 21

Line 26, "inducer-holing" should read --inducer-holding--.

Signed and Sealed this

Seventh Day of March, 2000

Attest:

Attesting Officer

Q. TODD DICKINSON

Commissioner of Patents and Trademarks